(12) United States Patent
Kleinert

(10) Patent No.: US 8,770,028 B2
(45) Date of Patent: Jul. 8, 2014

(54) METHOD FOR THE NONDESTRUCTIVE RECORDING OF A ROTATIONAL MOVEMENT OF A SPECIMEN, DEVICE THEREFOR AS WELL AS PROBE UNIT

(75) Inventor: Wolf-Dietrich Kleinert, Bonn (DE)

(73) Assignee: GE Sensing & Inspection Technologies GmbH, Hurth (DE)

( * ) Notice: Subject to any disclaimer, the term of this patent is extended or adjusted under 35 U.S.C. 154(b) by 780 days.

(21) Appl. No.: 12/665,700

(22) PCT Filed: Jun. 20, 2008

(86) PCT No.: PCT/EP2008/057888
§ 371 (c)(1),
(2), (4) Date: Apr. 27, 2010

(87) PCT Pub. No.: WO2009/015940
PCT Pub. Date: Feb. 5, 2009

(65) Prior Publication Data
US 2010/0199770 A1    Aug. 12, 2010

(30) Foreign Application Priority Data

Jun. 20, 2007  (DE) .......................... 10 2007 028 876

(51) Int. Cl.
*G01N 29/265* (2006.01)
*G01N 29/24* (2006.01)

(52) U.S. Cl.
USPC ............................................. 73/602; 73/634

(58) Field of Classification Search
USPC ........... 73/602, 618, 619, 620, 621, 633, 634, 73/644
See application file for complete search history.

(56) References Cited

U.S. PATENT DOCUMENTS 4,235,112 A    11/1980  Kaiser
5,538,004 A *  7/1996  Bamber ........................ 600/443
(Continued)

FOREIGN PATENT DOCUMENTS

DE    10 2004 059856 A1    6/2006
WO    WO02/086474 A        10/2002

OTHER PUBLICATIONS

International Search Report for PCT/EP2008/057888.
(Continued)

*Primary Examiner* — Peter Macchiarolo
*Assistant Examiner* — Rose M Miller
(74) *Attorney, Agent, or Firm* — McCarter & English, LLP

(57) ABSTRACT

The subject of the invention is a device for the nondestructive recording of a rotational movement, e.g. of a probe, on the surface of a specimen. In a developed configuration, a translational movement on the surface of the specimen can be detected. To this end, the device comprises a transmitter which is set up to transmit a temporal sequence of excitation signals Si, which penetrate into the specimen at least to some extent and interact with it. Furthermore, an array is provided, which is based on a plurality of receivers which are set up to receive echo signals, which result from the interaction of the excitation signals Si, transmitted by the transmitter, with the specimen. The echo signals for an excitation signal Si which are absorbed by the receivers form a set M (Si) of measurement values. Finally, an evaluation unit is provided, which is set up to determine a rotational movement of the device on the surface from a plurality of measurement value sets M (Si) which are correlated with temporally sequential excitation signals Si.

49 Claims, 13 Drawing Sheets

(56) References Cited

U.S. PATENT DOCUMENTS

| | | | |
|---|---|---|---|
| 2003/0158483 A1* | 8/2003 | Jackson et al. | 600/449 |
| 2003/0192382 A1* | 10/2003 | Mueller | 73/620 |
| 2004/0039312 A1* | 2/2004 | Hillstead et al. | 601/2 |
| 2006/0130587 A1* | 6/2006 | Howard et al. | 73/606 |
| 2009/0005679 A1* | 1/2009 | Dala-Krishna | 600/437 |

OTHER PUBLICATIONS

Horn, Berthold K.P., et al., "Determining Optical Flow", Articial Intelligence, Aug. 1981, pp. 185-203, vol. 16, No. 1-3.

Horn, Berthold K.P., "Determining Constant Optical Flow", © 2003.

\* cited by examiner

METHOD FOR THE NONDESTRUCTIVE
RECORDING OF A ROTATIONAL
MOVEMENT OF A SPECIMEN, DEVICE
THEREFOR AS WELL AS PROBE UNIT

CROSS-REFERENCE TO RELATED APPLICATIONS

This application is the U.S. National Phase of International Application No. PCT/EP2008/057888, entitled "Method for the Nondestructive Recording of a Rotational Movement of a Specimen, Device Therefor as well as Probe Unit," filed Jun. 20, 2008, which claims priority to German Patent Application No. 10 2007 028 876.1, filed Jun. 20, 2007, the disclosures of which are hereby incorporated by reference in their entireties.

BACKGROUND OF THE INVENTION

The subject of the present invention is a device for the nondestructive recording of a rotational movement on the surface of a specimen, a test unit which comprises such a device, as well as a method for the nondestructive recording of a rotational movement of a device on the surface of a specimen.

Particularly in the field of nondestructive material testing, for example by means of ultrasound or by means of eddy currents, a wide range of methods and devices are known from the prior art, with the aid of which it is possible to record structural characteristics of a specimen which for example can relate to the volume of the specimen or also to surfaces of the specimen and can for example pertain to imperfections, cracks, cavities, corroded surfaces, etc. Generally, the devices used for such testing purposes are based on suitable transmission and receiver units in the form of a probe assembly which generate test signals which are detected after an interaction with the specimen. The structure of the specimen in the spatial region investigated can then be deduced from the echo signals detected. If one displaces the probe assembly on the surface of the specimen during the testing method and records the structural characteristics of the specimen during the displacement in dependence on the probe position, then it is possible to create a spatial image of the interesting structural characteristics of the specimen.

The methods and devices used today to some extent achieve extraordinary accuracies when resolving the structural characteristics of the specimen investigated. However, the resolution achieved during the following of the movement of the probe on the surface remains far behind the resolution capability of the structure sensitive investigation methods used, such as e.g. an ultrasound pulse-echo method, in the vast majority of cases. This is due to the fact that until today only mechanical displacement transducers are used in practice for recording the movement of the probe on the surface of the specimen. Due to the principle used, these are affected with a relatively high measurement error. Furthermore, no systems have become known for a long time which would allow the recording of a rotational movement of the probe on the surface of the specimen.

SUMMARY OF THE INVENTION

This is where the present invention comes in, which has made its object to provide a method and a device for the recording of the movement of a device, for example of a probe, on the surface of a specimen, which works nondestructively and has an improved accuracy compared with the previously known methods and devices. Furthermore, the recording of rotational movements of the device on the surface of the specimen should be enabled.

This object is achieved by a device with the features of disclosed herein as well as by a method with the features of disclosed herein.

Furthermore, a test unit is disclosed herein, which is based on a device according to the invention, and also a special configuration of the device according to the invention of inherent inventive value is disclosed herein.

The method according to the invention works nondestructively and is provided to record a rotational movement of a device, for example of a probe on the surface of a specimen. In a preferred development, the method is in particular suitable for generally recording a movement of a device on the surface of a specimen, that is to say both with respect to its rotational and with respect to its translational degrees of freedom. The method comprises the following method steps in its simplest configuration:

a) transmission of a temporal sequence of excitation signals Si, which penetrate into the specimen at least to some extent and interact with it,
b) reception of echo signals, which result from the interaction of the excitation signals Si, transmitted by the transmitter, with the specimen, by means of an array which has a plurality of receivers, in the process, the echo signals which result from an excitation signal Si and are absorbed by the receivers form a set M (Si) of measurement values, and
c) determination of a rotational movement of the device on the surface of the specimen from a plurality of measurement value sets M (Si) (at least from two measurement value sets) which are correlated with temporally sequential excitation signals Si.

In connection with the present invention, a temporal sequence of excitation signals Si is generally understood to mean a sequence of, for example, pulsed signals which repeat with a regular temporal spacing. In particular, this can be a regular sequence of short ultrasound pulses. The method can on the other hand also stretch to continuous excitation signals, however. Essentially, in the context of the present invention, it depends on the fact that echo signals from the specimen are absorbed by means of the receiver in defined temporal spacings from one another. In the case of a continuous excitation signal, the echo signals could for example be absorbed in fixed time spacings of for example 40 milliseconds, which corresponds to 25 measurement value sets M (Si) per second. Furthermore, it is possible to synchronise the temporal sequence of the excitation signals with the temporal sequence of the echo signals received. If the excitation signal consists of a sequence of pulses, then the echo signal also consists of a sequence of pulses. These can be detected by mean of continually operating receivers for example and subsequently evaluated in the context of a time of flight (TOF) measurement (pulse-echo method).

The excitation signals which are used in the context of the method according to the invention should be of such a type in this case that they interact with structural characteristics of the specimen, such as for example geometric structures of a boundary surface or material inhomogeneities in the volume of the specimen. Examples for this are corroded surfaces and also inclusions or imperfections in the volume of the specimen such as cavities and cracks.

In a first preferred configuration of the method according to the invention, conclusions are drawn from the absorbed pulse echoes about the local structural characteristics of the specimen. If a receiver array is used, then given suitable method control, a spatial image of the structural characteristic of the specimen can be created immediately, e.g. a spatial representation of the local ultrasound reflectivity in the form of a C scan centred on the local position X0 of the receiver array. In the simplest case, an image of this kind is a reflection pattern which is similar to the "speckle pattern" known from the optic with coherent beams, which one gets from the reflection of a test beam on a spatial structure such as a rough surface.

If the receiver array is moved on the surface of the specimen into a new position X1, then a new image of the structural characteristics is created, centered on the new position X1, which image preferably partially spatially overlaps with the image created at the first position X0. The movement of the receiver array on the surface of the specimen can then be deduced using a comparison of the images at the positions X0 and X1. To do this, recourse can be had to a mathematical algorithm as is outlined below. At the same time, an overall image of the spatial distribution of the of the structural characteristics of the specimen (also used for the movement recording) can—but need not be—created from the movement data as well as the sequence of the images.

In a further preferred configuration of the method according to the invention, a plurality of images of the specimen are created at a test position X of the receiver array, at least one of which images is used as the basis for the previously described algorithm for determining the movement of the receiver array. Thus, the backwall echo of the specimen can be used for example in an ultrasound-based pulse-echo method in order to analyse the movement of the receiver array. Work is typically done here with the vertical intromission of sound. For creating an image of the spatial distribution of the structural properties of the specimen on the other hand, e.g., echo signals from the volume of the specimen, which were also obtained using angular intromission of sound for example, can also be used. Also, these echo signals do not necessarily have to trace back to the same excitation pulse, rather they can also be generated by means of a following pulse in a pulse sequence. In particular, the ultrasound characteristics of the intromitted ultrasound packet such as intromission angle or focal depth can be changed from pulse to pulse here.

The method according to the invention is particularly simple to carry out if the receivers which form the array are arranged lying in one plane. In this case, the array preferably comprises at least two linear arrangements of at least three receivers in each case, which receivers extend in various spatial directions. In an improved embodiment, the receivers which form the array are also arranged on grid points of a two-dimensional array, wherein at least three receivers are arranged in each of the two main directions of the grid.

Particular advantages result if at least one of the receivers of the array, in particular all receivers of the array however, are constructed in such a manner that in addition to their characteristic as a receiver, they can furthermore also be operated as a transmitter for transmitting the temporal sequence of excitation signals Si. Mention may be made by way of example for this of arrays of ultrasound transducers, as are known from the prior art, which ultrasound transducers can function both as ultrasound transmitters and as ultrasound receivers.

In addition to the previously mentioned ultrasound receivers, a multiplicity of other receivers can also be used as receivers, however, such as for example eddy current sensors, electric sensors, magnetic field sensors or even sensors for electromagnetic radiation such as light in the infrared, visible or ultraviolet wavelength range, as well as X-ray radiation. Suitable signal sources are accordingly used as transmitters.

As was already mentioned above, in a preferred configuration of the method according to the invention not only a rotational movement of the device on the surface of the specimen is recorded. Rather, in a further method step, a translational movement of the device on the surface of the specimen is additionally determined from the plurality of the measured value sets M (Si). In the preferred configuration of the method according to the invention, which results from the exemplary embodiment discussed below, the determination of the rotational movement of the device on the surface of the specimen is based on a determination, which is to be carried out in advance, of the translational movement of the device on the surface of the specimen.

In a further preferred development of the method according to the invention, an image of the spatial distribution of the structural characteristic of the specimen, to which structural characteristic the measurement method used, such as for example the refection of short ultrasound pulses, is sensitive, is created in a further method step from the recorded movement data of the measurement device on the surface of the specimen as well as the measurement value sets M (Si) recorded in the process. In the process, the image of the structural characteristic of the specimen created in this manner can advantageously be shown on a display unit.

In the context of the configurations of the present invention, among other things, the movement data obtained in the context of the method according to the invention as well as data about the structural characteristics of the specimen can advantageously be entered into a three-dimensional (for example CAD-based) model of the specimen. In this way, a three-dimensional representation of the structural characteristics of the specimen results, which is exceptionally suited to the recording of the measurement carried out.

The device according to the invention for the nondestructive recording of a rotational movement on the surface of a specimen, particularly of a rotational movement of the device itself, comprises:

a) a transmitter which is set up to transmit a temporal sequence of excitation signals Si, which penetrate into the specimen at least to some extent and interact with it. In this case, the observations already made with respect to the method according to the invention, particularly that it a continuous excitation signal can also be meant here, apply in connection with the transmission of a temporal sequence of excitation signals claimed here b) an array consisting of a plurality of receivers which are set up to receive echo signals, which result from the interaction of the excitation signals Si, transmitted by the transmitter, with the specimen. In the process, the echo signals which are absorbed by the receivers and are correlated with a common excitation signal Si form a set M (Si) of measurement values, and c) an evaluation unit which is set up to determine a rotational movement of the device on the surface from a plurality of measurement value sets M (Si) which are correlated with temporally sequential excitation signals Si (wherein there are at least two measurement value sets).

In a preferred development of the device according to the invention, the evaluation unit is furthermore set up to furthermore determine a translational movement of the device on the surface of the specimen in addition to the rotational movement of the device on the surface from the plurality of measurement value sets M (Si).

With respect to further advantageous configurations of the device according to the invention, reference is made to the subclaims, the details of which have essentially already been mentioned in connection with the method according to the invention.

Particular advantages furthermore result if the device according to the invention is used to construct a test unit which is provided for the spatially resolved determination of a structural characteristic of a specimen by means of nondestructive material testing. In this case, the test unit is set up to create an image of the spatial distribution of the structural characteristic of the specimen from the movement data of the device (for example of the probe) recorded by the device as well as the recorded measurement value sets M (Si). In particular, it is advantageous in this case if the movement data used relates to both the rotational and the translational movement of the device, for example that is to say of the probe, on the surface of the specimen.

In a preferred configuration, the test unit according to the invention is set up to show the image created of the spatial distribution of the structural characteristics of the specimen on a display unit, for example an LCD screen or also in a computer-generated printout.

A further device which is connected with the previously mentioned method as well as the device and the test unit by means of a common inventive idea is likewise provided for the nondestructive creation of an image of the spatial distribution of a structural characteristic of a specimen. This device comprises a first transmitter which is set up to transmit a temporal sequence of excitation signals P, which penetrate into the specimen at least to some extent and interact with a structural characteristic of the specimen. Mention may be made by way of example for this of an ultrasound transmitter which transmits a sequence of short ultrasound pulses which are coupled into the volume of the specimen and are completely or partially reflected at structural characteristics of the specimen, such as for example the boundary surfaces of the specimen or structures in the specimen such as imperfections, cavities, inclusions or cracks. Mention may also be made here of the fact that the temporal sequence of excitation signals P transmitted by the first transmitter can also be a continuous excitation signal in an extreme case.

Furthermore, the device according to the invention comprises a first receiver which is set up to absorb the excitation signals P transmitted by the first transmitter as echo signals after their interaction with the specimen. Furthermore, reference may be made to the example of ultrasound technology, in the context of which the first receiver would be constructed as an ultrasound receiver which is provided to absorb reflected ultrasound pulses and for example to deduce the position, the size and the structure of the reflecting structures in the specimen from time of flight (TOF) measurements as well as the measured intensity of the reflected ultrasound pulses.

Furthermore, the device according to the invention comprises a second transmitter which is set up to transmit a temporal sequence of excitation signals Si, which interact with the specimen, wherein an at least partial penetration of the excitation signals into the volume of the specimen is not absolutely necessary. Rather, an interaction of the excitation signals Si with the surface of the specimen, which has a certain structure, can also be sufficient. An array consisting of a plurality of second receivers which are set up to receive echo signals, which result from the interaction of the excitation signals Si, transmitted by the second transmitter, with the specimen, acts together with the second transmitter. In the process, the echo signals which are absorbed by the receivers and belong to a common excitation signal Si form a set M (Si) of measurement values in each case.

An evaluation unit is furthermore assigned to the second transmitter and the array of second receivers, which evaluation unit is set up to determine a movement of the device on the surface of the specimen from a plurality of measurement value sets M (Si), particularly from at least two measurement value sets, which are correlated with temporally sequential excitation signals of the second transmitter, wherein the movement of the device on the surface can particularly be described by translational and/or rotational degrees of freedom.

Finally, the device for the nondestructive creation of an image of the spatial distribution of a structural characteristic of a specimen comprises a visualisation unit, which is set up to create an image of the spatial distribution of a structural characteristic of the specimen from the movement of the device on the surface of the specimen recorded by the evaluation unit as well as from the echo signals received by the first receiver.

The second transmitter, the array (comprising the second receiver) and the evaluation unit can in this case for example be merged to form a functional unit and be based on the principle of an "optical mouse" for example. By implementing the method according to the invention in such a developed "optical mouse", it is in particular possible to also record a rotational movement of the mouse in addition to the recording of a translational movement known from the prior art. In a configuration of this type, the movement of a probe which comprises the first transmitter and the first receiver is therefore registered on the surface of a specimen while using an optical mouse preferably developed in accordance with the method according to the invention.

Further advantages and features of the method according to the invention, the device according to the invention as well as the test unit according to the invention result from the following exemplary embodiments. These relate by way of example to the field of ultrasound testing. It has however already been pointed out that, in addition, other nondestructive test methods such as eddy current measurements or measurements with piezoelectric sensors, magnetic field detectors or generally with detectors for electromagnetic radiation of a wide range of wavelengths (e.g. light in the visible, UV or IR spectral range, X-ray radiation and microwave radiation) can be used.

From an algorithm, the method according to the invention can be carried out and the evaluation unit of the device according to the invention can be implemented. In this case, the mathematical algorithm is shown exemplarily for the case of a rotation about the point of origin. For the person skilled in the art it is obvious however, that this special case can be generalised by a simple coordinate transformation to the case of a rotation about any desired point on the surface of the specimen.

Portable ultrasound detectors are often used in test applications. The objects to be tested can for example be welded steel parts such as steel pipes. The ultrasound detector can be coupled to the part by means of oil, water or a lubricating grease and the tester can guide the detector in various zig zag movements over the areas to be tested or continue it on from these areas. The areas to be tested can for example be weld seams or corroded backwalls. With a detector of this type, faults in the part and poor weld seams can be found. As the movement of the detector is random and indeterminate, it is often only possible with difficulty to image the faults found in relation to the dimensions and design features of the part as well as to the position of the probe. For parts with complex geometry (for example for pipes or T joints), the testing and recording of the coordinates of faults found in dependence on the position of the probe can be particularly difficult.

DETAILED DESCRIPTION OF EMBODIMENTS OF THE INVENTION

Figure 1:
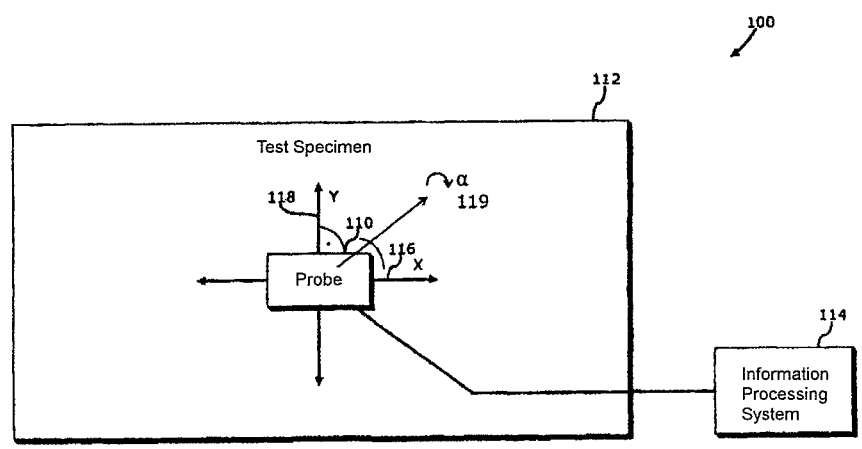
FIG. 1: shows a block diagram of a probe system according to one or a plurality of embodiments of this invention.

For reasons of simpler and/or clearer representation, the elements shown in the figures are not necessarily to scale. For clearer representation, for example, some elements may be shown enlarged in comparison with others. Common or similar elements are marked with identical reference numbers if appropriate in a number of figures.

In the following detailed description, numerous specific details are described in order to convey an in depth understanding of the subject of the claims. It is recognisable for the person skilled in the art, however, that the subject of the claims can also be implemented without these specific details. At other points, known methods, procedures, components and/or circuits were not described in detail.

In parts of the following detailed description, algorithms, programs and/or symbolic representations of operations are used, which are carried out for example in the memory of a computer on databits or binary digital signals. These algorithmic descriptions and/or representations can include methods used in data processing, with which the features of computer systems and/or other information processing systems, which operate with such programs, algorithms and/or symbolic representations of operations, are described.

A program and/or process can generally be considered as a self-consistent sequence of actions and/or operations which leads to a desired result. This includes the handling of physical quantities. These quantities are usually, but not necessarily, electric and/or magnetic signals which can be saved, transmitted, combined, compared and/or handled in some other manner. Generally, these signals are expressed as bits, values, elements, symbols, characters, terms, numbers and/or the like. It is pointed out, however, that these and similar terms must be linked with the corresponding physical quantities and that these are merely (generally expedient) descriptions of these quantities.

When terms such as processing, calculating, recording and/or similar terms are used in the following descriptions, reference is made, as long as nothing else is specified, to actions and/or processes of computers and/or computing systems and/or similar electronic computing devices, with which data, which is represented in the registries and/or memories of the computer and/or computing systems and/or similar electronic computing devices as physical or electronic quantities, is handled or transformed to other data which is represented as physical quantities in the memories, registries and/or similar elements of information storage, information transmitting and/or information display devices.

The claimed embodiments can include devices for carrying out the operations described here. These devices can be devices specifically designed for the respective application or all purpose computers which are selectively activated and/or reconfigured by a program saved on them. A program of this type can be saved on storage media such as diskettes, optical data carriers, CD-ROMs, magneto-optical data carriers, ROM read only memory, random access memory (RAM), EPROM read only memory, EEPROM read only memory, flash memory, magnetic and/or optical cards and/or other media types which are suitable for the saving of electronic instructions and/or can be coupled to a system bus of a computing device and/or other information processing system.

The processes and/or displays described here do not relate directly to a particular computing device and/or another device. Programs according to the invention can be used with various all purpose systems, but it can also be sensible to design a special device for the carrying out of the desired method. The desired structure for many such systems can be drawn from the following description. The embodiments are not described with reference to a particular programming language. Programs according to the invention can be implemented with various programming languages.

The expressions "coupled" and/or "connected" as well as related expressions are used in the following descriptions and/or claims. In one or a plurality of embodiments, the expression "coupled" can be used to specify that oil, water or a lubricating grease is located between the ultrasound probe and the test specimen. In certain embodiments, the expression "connected" can be used to specify that two or more elements have direct physical and/or electrical contact with one another. "Coupled" can mean that two or more elements have direct physical and/or electrical contact. "Coupled" can also mean that two or more elements have no direct physical and/or electrical contact, but cooperate or interact with one another, however. The expression "and/or" can have the following meanings: "and", "or", "exclusive or", "some but not all", "neither nor" and/or "both and". The subject of the claims is not limited in this respect, however.

FIG. 1 is a block diagram of a probe system according to one or a plurality of embodiments of this invention. The probe system 100 can comprise a probe 110 which can be moved over a surface of a test specimen 112, for example on a first axis (x axis) 116 and/or on a second axis (y axis) 118. Furthermore, the probe 110 can be rotated by an angle α about an axis 119 perpendicular to the x axis 116 and also the y axis 118, as is indicated by the arrow.

Figure 7:
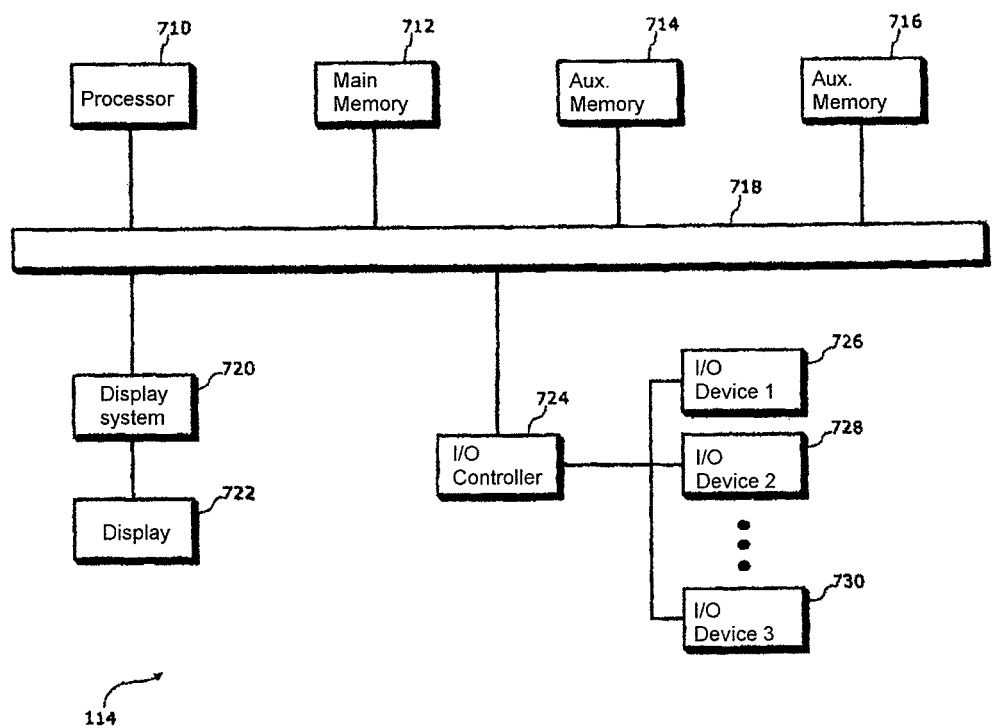
FIG. 7: shows a block diagram of an information processing system which can be used with a probe according to one or a plurality of embodiments of this invention

The probe 110 can comprise a transmitter and/or an array made up of one or a plurality of detector elements. The probe 110 can be coupled to an information processing system 114, for example in order to supply the probe 110 with operating power and/or control signals and/or in order to receive data which was recorded with the probe 110—for example using the sensor array. Example arrays of the probe 110 are shown in the FIGS. 2, 3 and/or 4 and explained in the corresponding descriptions. An example for an information processing system 114 is shown in FIG. 7 and explained in the corresponding description. In one or a plurality of embodiments, three or more measurement values per axis to be encoded can be recorded if the probe is not moved. The direction of the movement on the axis to be encoded can be calculated on the basis of three or more of such measurement values. These measurement values can change if the probe is moved. For example, the material noises or the remaining wall thickness of a corroded test specimen can be different at every position of the probe. The subject of the claims is not limited in this respect, however.

In one or a plurality of embodiments, the probe system 100 can be used to test the test specimen 112, for example in order to determine faults and/or defects in the test specimen 112. In such an example, the test specimen 112 can comprise a manufactured part such as for example a pipe, a T joint or an aircraft part such as a part of an aircraft engine, fuselage or wing. The probe system 100 can be laid out in such a manner that it is suitable for testing test specimens 112 with different topologies and/or geometries. In a certain embodiment, the test specimen 112 can comprise an organ, vessel and/or other tissue of a patient, for example of a mammal, wherein the probe system 100 is used in a medical application. The probe 110 and/or the probe system 100 can be laid out for the respective application of the probe system 100 with respect to size, shape and/or other features, including but not limited to the testing of manufactured parts, medical and/or surgical applications or the like. Here, one is only concerned with example applications for use of the probe system 100. The subject of the claims is not limited in this respect.

In one or a plurality of embodiments, the information processing system 114 can comprise a memory which contains a data file, which corresponds to the test specimen 112 to be tested with the probe system 100, but this is not necessary. If the test specimen 112 is a manufactured part for example, the memory of the information processing system 114 can contain a CAD (computer aided design) file or the like, wherein this is an electronic representation of the test specimen 112 which is used for design or manufacturing purposes. The CAD file is only one example for a file type and is not required. Instead of a CAD file, other graphics or image files can be used. The subject of the claims is not limited in this respect. In one or a plurality of embodiments, a CAD file of such a type can comprise a two dimensional representation of the test specimen 112, and in one or a plurality of embodiments, a CAD file of such a type can comprise a three-dimensional representation of the test specimen 112. The subject of the claims is not limited in this respect, however.

Figure 8:
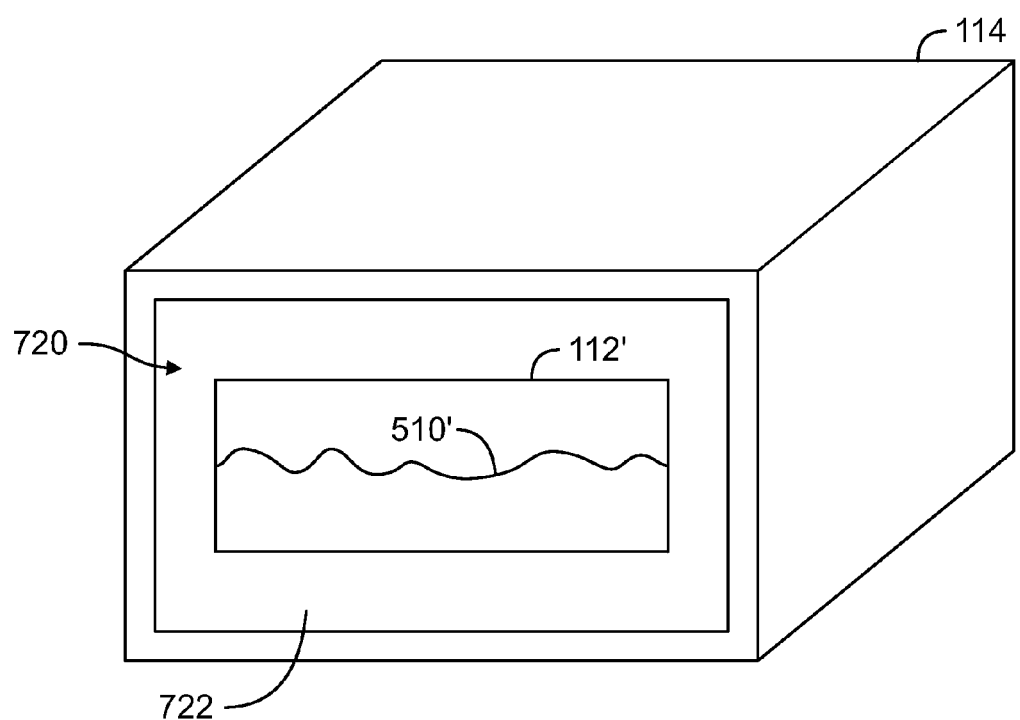
FIG. 8: shows an information processing system displaying an image of a feature of a test specimen within a created image of the test specimen as designed or manufactured.

In one or a plurality of embodiments, of which FIG. 8 is an example, the information processing system 114 can display the CAD file during the testing of the test specimen 112 by the probe system 100 as an image 112' on a display 722 coupled to the information processing system 114. At the same time, the information processing system 114 can display image data of the test specimen 112 which is recorded by the probe 110 as an image 510' on the display. Thus, the information processing system 114 can for example correlate data of the test specimen 112 recorded by the probe 110 with data of the test specimen 112 contained in the CAD file. The operator, who moves the probe 110 of the probe system 100 for example along the test specimen 112 can use a correlation of this type during the navigation as a reference for the area to be tested and/or the feature to be tested. If the operator finds a fault and/or defect at a certain position of the test specimen 112, they can record this position on the basis of the construction data for the test specimen 112 saved in the CAD file. This test data can be assigned to the data of the test specimen 112 for later use and/or investigation. In one or a plurality of embodiments, the operator can save a labelling in the CAD file of the position of a fault and/or defect and/or another noteworthy feature of the test specimen 112 found. Here, one is only concerned with example applications for use of the probe system 100. The subject of the claims is not limited in this respect.

Figure 2:
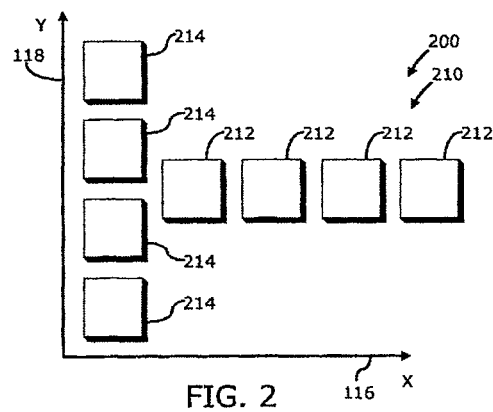
FIG. 2: shows a diagram of a sensor-array arrangement of a probe according to one or a plurality of embodiments of this invention.

FIG. 2 is a diagram of a sensor-array arrangement of a probe according to one or a plurality of embodiments of this invention. As shown in FIG. 2, the array 200 of sensor elements 212 and/or 214 on the probe 110 can be positioned in order to record features of the test specimen 112. In one embodiment, the sensor elements can comprise ultrasound detectors, GMI detectors (giant magneto impedance), piezoelectric sensors, hall sensors, eddy current sensors or other suitable sensor elements or the like. In one or a plurality of embodiments, the probe 110 can comprise a transmitter which transmits energy, signals, pulse and/or impulses which can be recorded by one or a plurality of sensors 212 and/or 214 of the array 200. These transmissions can take place at different times and be of different duration, form and/or pulse width. In one or a plurality of embodiments, these transmissions can for example comprise pulse forms and in one or a plurality of alternative embodiments, these transmissions can comprise forms and/or pulses in accordance with the Dirac delta function. The subject of the claims is not limited in this respect, however. The transmitted signals can also be high-frequency signals. In one or a plurality of embodiments, the operating frequency range of the probe 110 can lie between approx. 1 MHz and 25 MHz, for example when treating steel parts or the like or for penetrating the material of the test specimen 112. In one or a plurality of embodiments, a precision of the probe 110 can lie under 1 millimeter and/or under 100 micrometers, for example in dependence on the modality and/or frequency of the probe 110. In medical applications, the probe 110 can comprise a catheter tip or the like so that vessel walls can be investigated. Deviations of a recorded pattern of a vessel wall from the internal surface of the vessel wall can be recorded and optionally linked to a previously recorded image file of the vessel. This image file can for example be a three-dimensional image file which was recorded using magnetic resonance imaging, computed tomography or a similar method. By linking the deviations recorded to the image data, the position of a feature or an abnormality can be determined more accurately. The subject of the claims is not limited in this respect, however.

In one embodiment, the array 200 can comprise a first arrangement 210 of sensor elements 212 and/or 214, wherein in the first arrangement 210 a first sensor row 212 can be positioned on the axis 116, in order to record the movement of the probe 110 for example and/or in order to take images or other data of the test specimen 112 on the axis 116, and wherein a second sensor row 214 can be positioned on the axis 118 in order to record the movement of the probe 110 for example and/or to take images or other data of the test specimen 112 on the axis 118. The arrangement 210 of the array 200 shown in FIG. 2 can generally have a T shape or a similar shape. In one or a plurality of alternative embodiments, variations of the arrangement 210 of the array 200 can have an x shape or a similar shape, wherein for example some of the sensors 212 are arranged on one side of the sensor row 214 and some of the sensors 212 are arranged on another side of the sensor row 214. Here, one is only concerned with exemplary embodiments of the arrangement 210 of the array 200. The subject of the claims is not limited in this respect.

Figure 3:
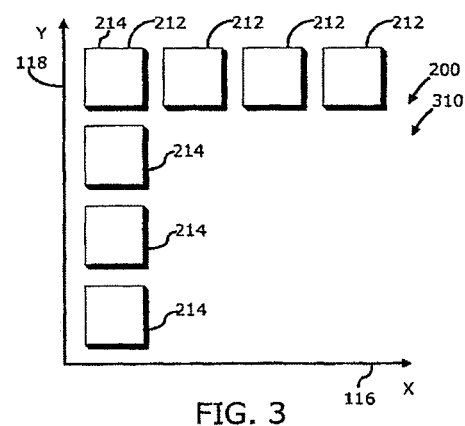
FIG. 3: shows a diagram of an alternative sensor-array arrangement of a probe according to one or a plurality of embodiments of this invention.

FIG. 3 is a diagram of an alternative sensor-array arrangement of a probe according to one or a plurality of embodiments of this invention. As is shown in FIG. 3, the arrangement 310 of the array 200 of sensors 212 and/or 214 can have an L shape or a similar shape. In the case of such an arrangement and/or variants of such an arrangement, one or a plurality of sensors in a first sensor row 212 can also comprise a sensor which belongs to a second sensor row 214, so that at least one of the sensors is operated in such a manner that a movement of the probe 110 and/or an image and/or other data of the test specimen 112 in a first direction on the axis 116 and/or in a second direction on the axis 118 can be recorded. The subject of the claims is not limited in this respect, however.

Figure 4:
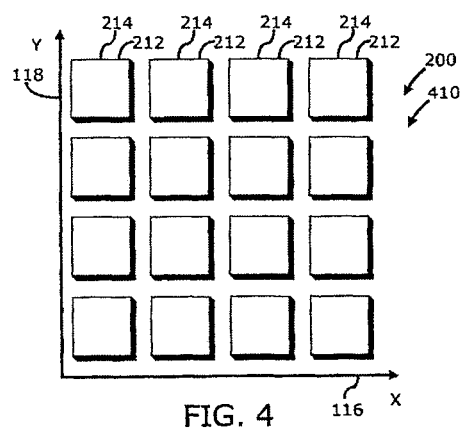
FIG. 4: shows a diagram of a further alternative sensor-array arrangement of a probe according to one or a plurality of embodiments of this invention.

FIG. 4 is a diagram of a further alternative sensor-array arrangement of a probe according to one or a plurality of embodiments of this invention. As is shown in FIG. 4, the arrangement 410 of the array 200 can comprise a 4 by 4 grid of sensors 212 and/or 214. The arrangement 410 in FIG. 4 comprises a single 4 by 4 grid of sensors, but other arrangements can also be used, for example, sensors can be positioned in a 1 by 2 grid, a 1 by 16 grid, a 1 by 128 grid, an 8 by 8 grid and/or in any desired other arrangement. The arrangements 210, 310 and/or 410 of the array 200 shown in FIG. 2, FIG. 3 and/or FIG. 4 are merely example arrangements of the array 200. The subject of the claims is not limited in this respect.

Figure 5:
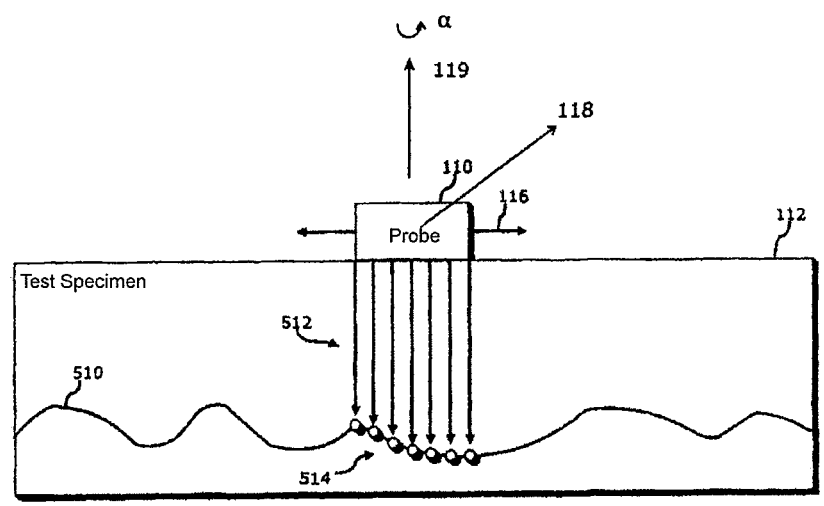
FIG. 5: shows a diagram of a probe according to one or a plurality of embodiments of this invention which is used to determine a feature (in this example corrosion) of a test specimen.

FIG. 5 is a diagram of a probe according to one or a plurality of embodiments of this invention which is used to determine a feature of a test specimen. As is shown in FIG. 5, the probe 110 can be moved on the axis 116, for example along the test specimen 112. For reasons of simplification FIG. 5 only shows a main axis (here the x axis 116) of the array which should be used in accordance with the method according to the invention or which is comprised by the device according to the invention. An analogous image, which is obvious for the person skilled in the art, results in a second main direction (here e.g. the y axis 118) which is independent of the first main direction and is not shown here. Furthermore, the probe 110 can be rotated on the surface of the test specimen 112 by an angle α about the axis 119 which is perpendicular to the two previously mentioned axes 116, 118.

The probe 110 can emit a signal 512 which at least partially penetrates the test specimen 112. In one or a plurality of embodiments, the signal 512 can be reflected at least partly from the feature 510 of the test specimen 112 with the probe 110 still, for example as an echo signal, so that three or more values per axis can be recorded and encoded. In one or a plurality of embodiments, the signal 512 can be reflected at least partly from the feature 510 and penetrate it at least partly, but the probe 110 can record the feature 510 for example on the basis of a part of the signal 512 reflected form the feature 510, and an image 510' of the feature 510 can be shown. In one or a plurality of embodiments, a signal intensity and/or a signal strength of the signal 512 can be adjusted and/or a frequency of the signal 512 can be set in order to achieve a desired penetration depth of the signal 512 through the test specimen 112, so that the feature 510 can be reliably recorded and/or an image 510' can be shown, for example, as depicted in FIG. 8. In one or a plurality of embodiments, the feature 510 can for example comprise a manufacturing defect and/or a fault, a cavity, a stress, a crack, a breakage, a layer, an inclusion and/or—in the case of metallic or similar test specimens 112—a corrosion. The subject of the claims is not limited in this respect, however. If the probe 110 is moved on the axis 116, the probe 110 can record one or more data points 514 and in a particular embodiment, the probe 110 can record three or more data points which correspond to the feature 510 and are recorded at regular time intervals. Due to the movement of the probe 110 on the axis 116 along the test specimen 112, the probe 110 can record data from which positional data, speed data, image data and/or other data can be recorded. This data can optionally be transferred to the information processing system 114 where it can be saved, handled, processed, transferred and/or displayed for example, as seen in FIG. 8. Using the probe 110, data pertaining to loose material in the test specimen 112 can be recorded and converted into an image 510' which is then displayed on a display 722 of an information processing system 114. On the basis of such an image, the operator can undertake a visual inspection of the test specimen 112 and/or navigate the test specimen 110 visually on the axis 116 of the test specimen 112, wherein an image can be used for example for documentation of the test. The subject of the claims is not limited in this respect, however.

In one or a plurality of embodiments, the probe system 100 can be used for example for finding corrosion in the test specimen 112. The array 200 can comprise an 8 by 8 array of sensors. A virtual probe which comprises four elements for example can be scanned along a first area of the array 200, for example along 4 by 8 elements. Scanning of this type can be undertaken electronically and take place in the y direction on the axis 118, then displaced around an element in the x direction on the axis 116 and subsequently continued in the y direction. A multidimensional scanning (C scan) can be created. A C scan of this type can be produced from an echo of the signal 512 which is reflected from the feature 510 for example if the feature 510 is corrosion in the test specimen 110. The coordinates of a displacement of this type can be recorded for example in that a plurality of C scans created with the probe 110 still and/or with the probe 110 moved along the test specimen 112 are compared with one another.

Alternatively, the probe 200 can also be moved on the surface of the test specimen 112, wherein both a translational and a rotational movement of the probe 200 is possible.

In one or a plurality of embodiments, this method can resemble a movement recognition method used in the case of optical mice and the first area of the array can be used for positional data. Another element of the probe can be used for measuring corrosion. In one or a plurality of embodiments, the same area of an array can be used for positional data and measurement data (for example corrosion). A broad-scale C scan of the corrosion can be recorded on the basis of the positional data recorded by means of the scanning operation of the probe 110 as well as the corrosion data recorded with the second element of the probe. The subject of the claims is not limited in this respect, however. In one or a plurality of embodiments, the first probe can comprise a first area of the array 200 and the second probe can comprise a second area of the array 200. Alternatively, the first probe can comprise a first array and the second probe can comprise a second array. The subject of the claims is not limited in this respect, however.

In one or a plurality of alternative embodiments, all or almost all elements of the array can receive echoes of the signal 512 at the same time and be received by individual sensors 212 and/or 214 of the array 200. A C scan can be created from such echo signals which are reflected back from the corrosion of the feature 410 for example with the probe still and/or with the probe moved on the axis 116 along the test specimen 112. The C scans can be compared with subsequent scans, which are created with the probe 110 moved on the axis 116, for creating positional coordinates. A similar method to in the case of optical mice can be used here. In the case of such an arrangement, the same array can be used as a dual probe for recording positional data and/or for recording data for the corrosion feature 510. The subject of the claims is not limited in this respect, however.

In one or a plurality of embodiments, the scan data recorded with the probe 110 can optionally be displayed as an image 510' on a display of an information processing system 114, for example when operating the probe system 100. So an image 510' of the area scanned with the probe 110 can be displayed on the display 722 (block 622), so that the operator can see it and use it when navigating the probe 110 along the test specimen 112. The file of the test specimen 112 can optionally be compared with scan data (block 624) which was recorded with the probe 110. So, for example, an electronic version or image 112' of the test specimen represented in the CAD file can be laid over an image 112' of the test specimen 112 recorded with the probe 110, so that, for example, a correlation between a feature of the test specimen 112 and one or a plurality of coordinates of the position of the probe 110 and of the test specimen 112 can be recorded from the CAD file. It can be recorded whether the test specimen 112 has a certain feature, for example the feature 510 (block 626). This feature can comprise a manufacturing defect and/or a fault, a cavity, a stress, a crack, a breakage, a layer, an inclusion and/or—in the case of metallic or similar test specimens 112—a corrosion. The feature can for example be recorded in that the operator of the probe system 100 carries out a visual inspection which is based at least in part on an image 510' of the test specimen 112 recorded with the probe 110. Alternatively, the feature can at least partly be recorded on the basis of software programming executable by means of the information processing system 114.

Figure 6:
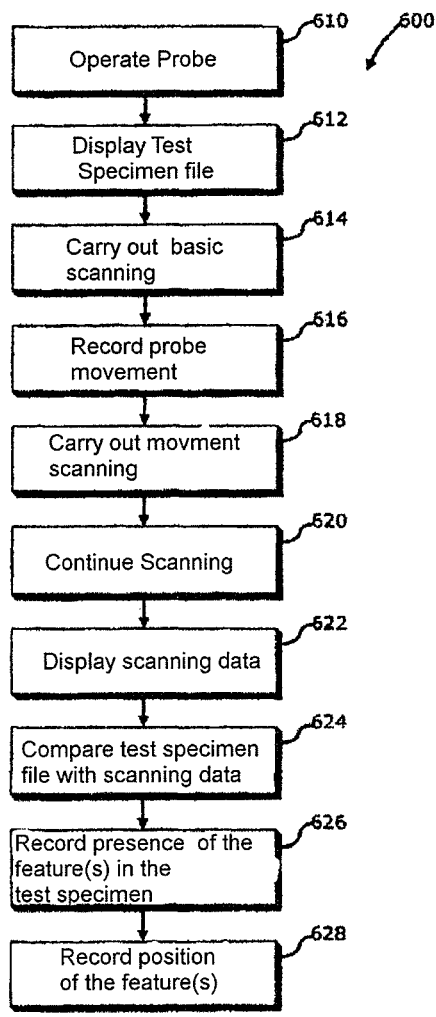
FIG. 6: shows a flow diagram of a method of operating a probe according to one or a plurality of embodiments of this invention.

FIG. 7 is a block diagram of an information processing system which can be used with a probe according to one or a plurality of embodiments of this invention. The information processing system 114 shown in FIG. 1 and/or FIG. 7 can be used in order to offer access to a computer program and/or a graphical user interface in that hardware components are provided, on which the computer program and/or the graphical user interface 110 can be executed, in order to carry out the method 600 from FIG. 6, for example. A computer program of this type and/or machine-readable instructions of this type can be saved on a computer- or machine-readable medium such as a CD (Compact Disc), a DVD (Digital Versatile Disc), a flash memory device, a hard drive, etc. As is shown in FIG. 7, the information processing system 114 can be controlled by the processor 710. The processor 710 can comprise a central unit such as a microprocessor or microcontroller which is used for executing programs, for handling data and for controlling the tasks of the information processing system 114. The communication with the processor 710 can be implemented using a bus 718 which is used for transmitting data between the components of the information processing system 114. The bus 718 can comprise a data channel for transmitting data between memory components and other peripheral components of the information processing system 718. The bus 718 can furthermore provide a group of signals which are used for communication with the processor 710, for example a data bus, an address bus and/or a control bus. The bus 718 can have a bus architecture in accordance with established standards such as ISA (Industry Standard Architecture), EISA (Extended Industry Standard Architecture), MCA (Micro Channel Architecture), PCI (Peripheral Component Interconnect) as well as in accordance with IEEE standards (Institute of Electrical and Electronics Engineers) such as for example IEEE 488 GPIB (General-Purpose Interface Bus) and IEEE 696/S-100. The subject of the claims is not limited in this respect, however.

Other components of the information processing system can for example comprise the main memory 712 and/or auxiliary memory 714. The information processing system 114 can furthermore have an auxiliary processor 716, which may be a further processor such as for example a digital signal processor. The main memory 712 can be used for storing instructions and data for programs which are executed by the processor 710. The main memory 712 can be semiconductor-based memories such as DRAM (Dynamic Random Access Memory) and/or SRAM (Static Random Access Memory) and/or the like. Other types of semiconductor-based memory are for example SDRAM (Synchronous Dynamic Random Access Memory), RDRAM (Rambus Dynamic Random Access Memory) and FRAM (Ferroelectric Random Access Memory). The auxiliary memory 714 can be used for storing instructions and/or data which are loaded into the main memory 712 before execution. The auxiliary memory 714 can be semiconductor-based memories such as for example ROM (Read-Only Memory), PROM (Programmable Read-Only Memory), EPROM (Erasable Programmable Read-Only Memory), EEPROM (Electrically Erasable Read-Only Memory) and/or flash memory and/or block oriented memory (similar to EEPROM). The auxiliary memory 714 can additionally be semiconductor-based memories including, but not limited to magnetic tape, drum storage, diskette, hard drive, optical data carriers, laser disc, CD-ROM (Compact Disc Read-Only Memory), CD-R (Write Once Compact Disc), CD-RW (Rewritable Compact Disc), DVD-ROM (Digital Versatile Disc Read-Only Memory), DVD-R (Write Once DVD), DVD-RW (Rewritable Digital Versatile Disc) etc. Other types of memory devices can also be used. The information processing system 114 optionally comprises an auxiliary processor 716 which can be an auxiliary processor for managing the input and output; and auxiliary processor for executing floating point operations; a digital signal processor and/or a special microprocessor, the architecture of which is suitable for the fast execution of signal processing algorithms; a processor connected downstream and/or subordinated to the processor 710; an additional microprocessor and/or controller for two- or multi-processor systems and/or a coprocessor and/or an additional processor. Auxiliary processors of this type can be discrete processors and/or processors integrated into the same subassembly as the processor 410, for example into a multicore and/or multithread processor. The subject of the claims is not limited in this respect, however.

The information processing system 114 can additionally comprise the following: a display system 720 for connecting the display 722, an input/output controller 724 for connecting input/output devices such as for example I/O device 726, I/O device 728 up to an nth I/O device 730. The display system 720 can comprise a graphics card which has components for controlling the display 722, for example graphic memory, buffer memory and/or a graphics engine. The graphics memory can for example be VRAM (Video Random Access Memory), SGRAM (Synchronous Graphics Random Access Memory), WRAM (Windows Random Access Memory) and/or the like. The display 722, as shown, for example, in FIG. 8, can comprise the following: a cathode ray tube display such as a monitor or television and/or alternative types of display technologies such as a cathode ray tube projector, an LCD projector (Liquid-Crystal Display), an LCD display, an LED display (Light-Emitting Diode), a gas and/or plasma display, an electroluminescent display, a vacuum fluorescent display, a cathode luminescent and/or field emission display, a PALC display (Plasma Addressed Liquid Crystal), a HGED display (High Gain Emissive Display) and so on. The input/output controller 724 can comprise one or a plurality of controllers and/or adapters which provide interface functions for the I/O device 726, the I/O device 728 and/or the I/O device 730. The input/output controller 724 can comprise the following: a serial connection, a parallel connection, a USB connection (Universal Serial Bus), a serial IEEE 1394 bus connection, an infrared connection, a network adapter, a printer adapter, a high-frequency communication adapter, a UART connection (Universal Asynchronous Receiver-Transmitter) and/or similar components which provide an interface to I/O devices such as the following: keyboard, mouse, trackball, touchpad, joystick, trackstick, infrared converter, printer, printer, modem, wireless modem, barcode reader, CCD reader (Charge-Coupled Device), scanner, CD (Compact Disc), CD-ROM (Compact Disc Read-Only Memory), DVD (Digital Versatile Disc), video recording device, TV card, touch-screen, stylus, electroacoustic transducer, microphone, loud-speaker, audio amplifier and/or the like. The input/output controller 724 and/or the I/O device 726, the I/O device 728 and/or the I/O device 730 can provide and/or receive analogue and/or digital signals for communication between the information processing system and external devices, networks and/or information sources. The input/output controller 724 and/or the I/O device 726, the I/O device 728 and/or the I/O device 730 can be used for the implementation of industry-standard architectures, for example Ethernet IEEE 802 standards such as IEEE 802.3 for broadband and/or baseband networks, IEEE 802.3z for Gigabit Ethernet, IEEE 802.4 for token passing bus networks, IEEE 802.5 for token ring networks, IEEE 802.6 for metropolitan area networks (MAN) and/or the like, fibre channel, DSL (Digital Subscriber Line), ADSL (Asymmetric Digital Subscriber Line), frame relay, ATM (Asynchronous Transfer Mode), ISDN (Integrated Digital Services Network), PCS (Personal Communications Services), TCP/IP (Transmission Control Protocol/Internet Protocol), SLIP/PPP (Serial Line Internet Protocol/Point-to-Point Protocol) and so on. The information processing system 114 in FIG. 7 is only one example for an information processing system and/or a computer platform. The subject of the claims is not limited in this respect.

Optical flow was developed for evaluation of pixel based picture movement. This method can be applied to all kind of different measurements if a "pixel-like" measurement array can be obtained from a measurement sensor array as long as the measurement values are changing when the sensor array is moved. Examples of possible measurement values include: wall thickness, surface structure (optical or acoustical), material noise, Eddy Current results, etc. For the optical flow theory an additional constraint is needed to solve the equations. In this pitch constraint equations are developed to calculate translation in x and y direction and rotation of the sensor array using two successive sets of measurement values. A precondition for the constraint equations is that the measurement values do not changing with a fixed sensor array (except for the measurement error).

Figure 9:
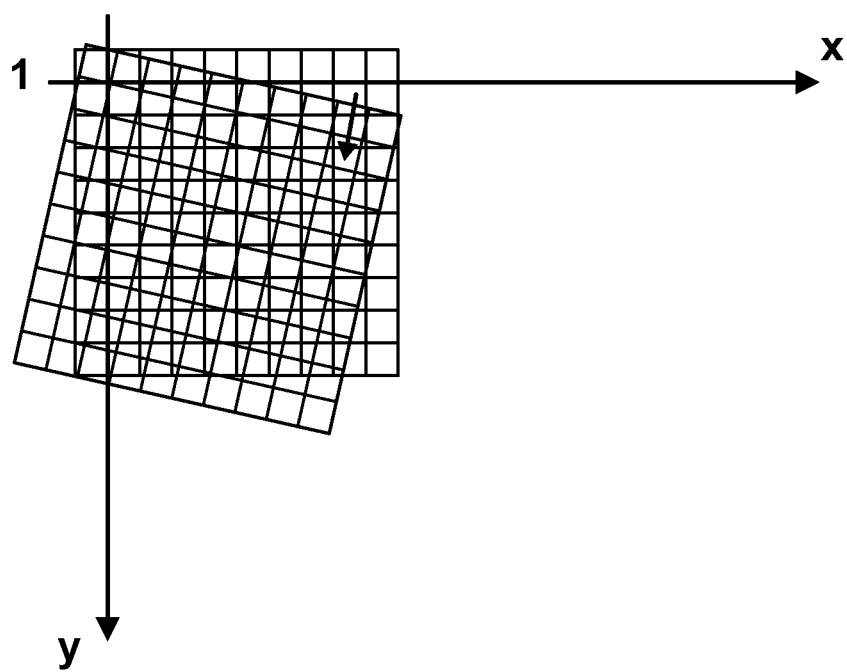
FIG. 9: shows a graphical depiction of rotation of a measurement array.

FIG. 9 is a graphical depiction of rotation of a measurement array. The graph of FIG. 9 includes an arrow (vector) showing the movement of one sensor as an example from time $t_1$ to time $t_2$. The time difference between $t_1$ and $t_2$ is the time interval between measurements, which will be constant during the manual movement of the sensor array. The components of this vector in x and y direction will be used. The movement of the sensor array can always be reduced to a rotation by an angle θ and a translation in the direction of the x-axis and y-axis.

Figure 10:
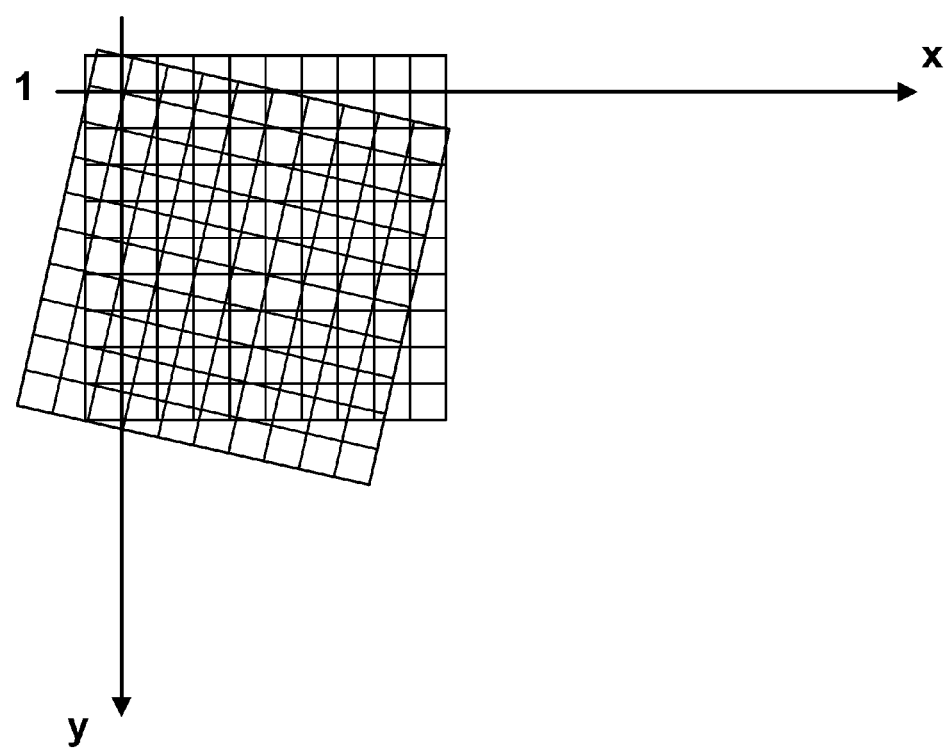
FIG. 10: shows a graphical depiction of rotation of a sensor array.
Figure 11:
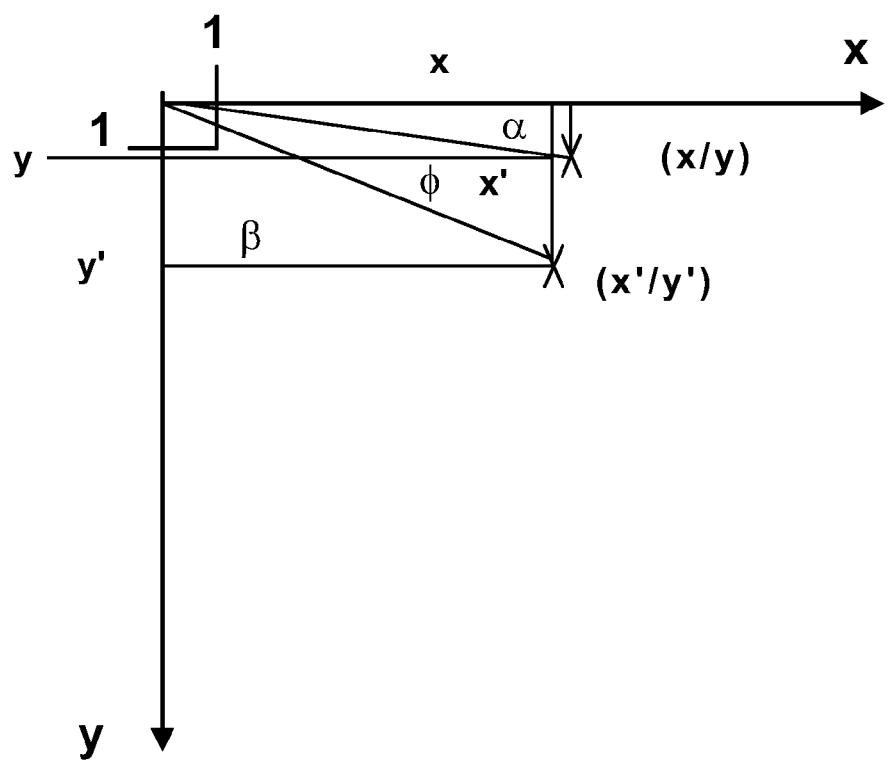
FIG. 11: shows a graphical depiction of rotation of a single point.

FIG. 10 is another graphical depiction, here, of rotation of the sensor array. FIG. 11 is a further graphical depiction, of rotation of a single point. The following equations correlate to FIG. 11:

$$\alpha + \beta + \phi = 90° \Rightarrow \beta = 90° - (\phi + \alpha)$$

And the additional theorems:

$$\sin[90° - (\varphi + \alpha)] = \frac{x'}{\sqrt{x^2 + y^2}} \Rightarrow \sin 90° \cos(\varphi + \alpha) + \cos 90° \sin(\varphi + \alpha) = \frac{x'}{\sqrt{x^2 + y^2}}$$

$$\Rightarrow \cos(\varphi + \alpha) = \frac{x'}{\sqrt{x^2 + y^2}} \Rightarrow \cos\varphi\cos\alpha - \sin\varphi\sin\alpha = \frac{x'}{\sqrt{x^2 + y^2}}$$

$$\Rightarrow \cos\varphi \frac{x}{\sqrt{x^2 + y^2}} - \sin\varphi \frac{y}{\sqrt{x^2 + y^2}} = \frac{x'}{\sqrt{x^2 + y^2}} \Rightarrow x' = x\cos\varphi - y\sin\varphi$$

equivalent for y': y'=x sin φ+y cos φ
From the sketch:

$$\sin\alpha = \frac{y}{\sqrt{x^2 + y^2}} \quad \sin\beta = \frac{x'}{\sqrt{x^2 + y^2}}$$

$$\cos\alpha = \frac{x}{\sqrt{x^2 + y^2}} \quad \cos\beta = \frac{y'}{\sqrt{x^2 + y^2}}$$

Figure 12:
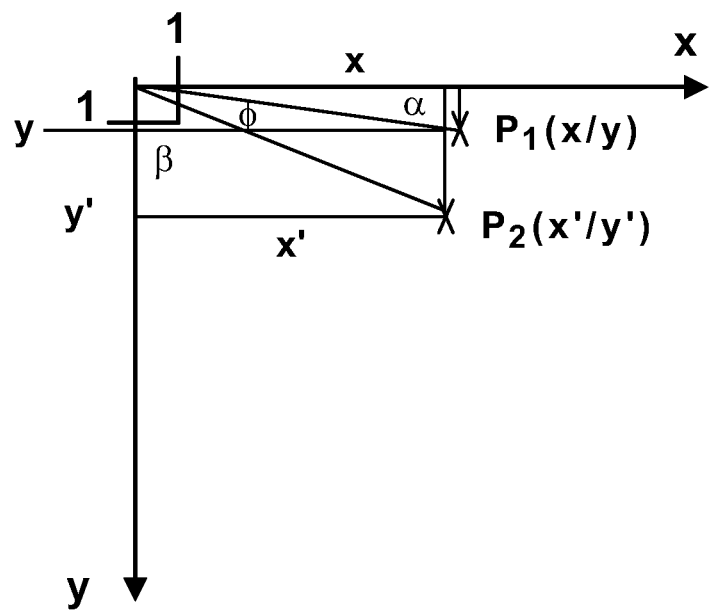
FIG. 12: shows a graphical depiction of rotation of a single point between point $P_1$ and point $P_2$.

FIG. 12 is a graphical depiction of rotation of a single point between point $P_1$ and point $P_2$. The following equations relate to FIG. 12:

$$u=x'-x \text{ and } v=y'-y \Rightarrow$$

$$u=x \cos \phi-y \sin \phi-x \text{ and}$$

$$v=x \sin \phi+y \cos \phi-y \Rightarrow$$

$$u=x(\cos \phi-1)-y \sin \phi \text{ and}$$

$$v=y(\cos \phi-1)+x \sin \phi \Rightarrow$$

Figure 13:
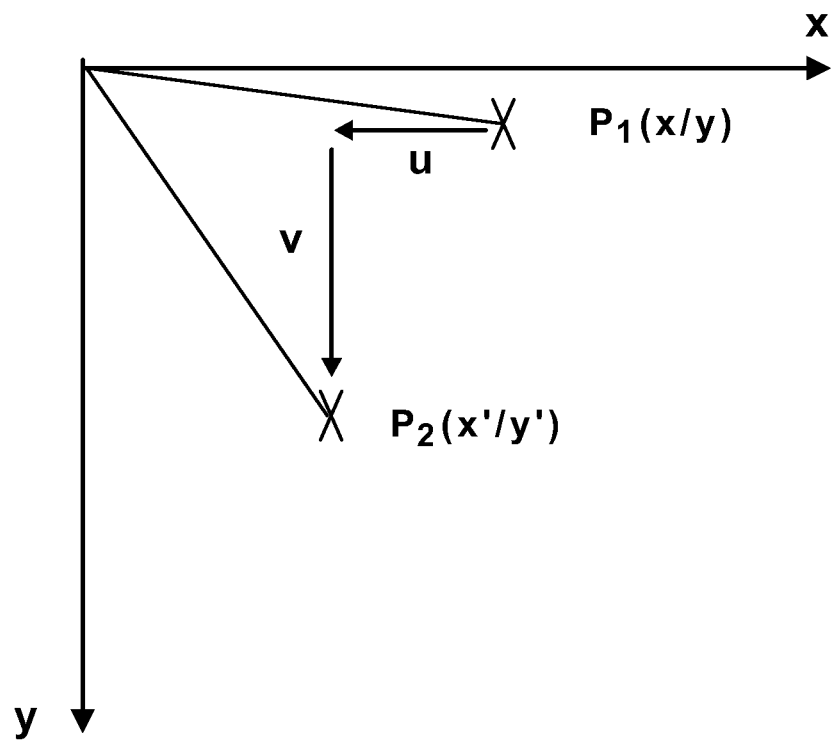
FIG. 13: shows a graphical depiction of rotation and translation of a single point between point $P_1$ and point $P_2$.

Additionally, as shown in FIG. 13, depicting rotation and translation ($x_0$ and $y_0$) of a single point between point $P_1$ and point $P_2$, the constraint equations (1) and (2) are:

$$u = x(\cos\phi - 1) - y\sin\phi + x_0 \quad (1)$$

$$v = y(\cos\phi - 1) + x\sin\phi = y_0 \quad (2)$$

The so called "Brightness" Equation from the Theory of Optical flow is used, but instead of brightness all other measurement values (e.g., wall thickness, surface structure, material noise, Eddy Current results, etc.) can be used as long as the measurement values are not changing with a fixed sensor array (except error of measurement).

In constraint equation (3), E is the measurement value used. E will be dependent on the x and y position and the time t between two measurements (See "Determining Optical Flow," Berthold K. P. Horn, et al., Artificial Intelligence 17 (1981), p. 185-203):

$$\frac{\partial E}{\partial x}\frac{dx}{dt} + \frac{\partial E}{\partial y}\frac{dy}{dt} + \frac{\partial E}{\partial t} = 0 \quad (3)$$

The following abbreviations are introduced:

$$E_x = \frac{\partial E}{\partial x} \; E_y = \frac{\partial E}{\partial y} \; E_t = \frac{\partial E}{\partial t}$$

and $$u = \frac{dx}{dt} \; v = \frac{dy}{dt}$$

In the "Brightness" Equations from the Theory of Optical Flow and Constraint Equations as already defined, the constant time difference $t_2 - t_1$ between two successive measurements of the sensor array is defined as time unit one. In this case, the movement of the sensor as defined in the constraint equations can be used as the velocities u and v in the "Brightness Equation":

$$E_x\{x(\cos\varphi - 1) - y\sin\varphi + x_0\} + E_y\{y(\cos\varphi - 1) - x\sin\varphi + y_0\} + E_t =$$
$$0 \Leftrightarrow (E_x x + E_y y)(\cos\varphi - 1) + (E_y x - E_x y)\sin\varphi + x_0 E_x + y_0 E_y + E_t = 0$$

With the following abbreviations to arrive at equation (4):

$$A = E_x x + E_y y \text{ and} \quad (4)$$
$$B = E_y x - E_x y \Rightarrow A(\cos\varphi - 1) + B\sin\varphi + x_0 E_x + y_0 E_y + E_t = 0$$

$E_x$, $E_y$ and $E_t$ are numerically derived as described in "Determining Optical Flow" by B. Horn and G. Schunck. The examples below in Tables 1-5 are derived from a simulated wall thickness measurement on a corroded plate.

TABLE 1

| First Measurement | | | | | | | | | |
|---|---|---|---|---|---|---|---|---|---|
| 4.93 | 4.95 | 4.96 | 4.98 | 5.00 | 5.02 | 5.04 | 5.05 | 5.07 | 5.09 |
| 4.94 | 4.95 | 4.97 | 4.98 | 5.00 | 5.02 | 5.03 | 5.05 | 5.06 | 5.08 |

TABLE 1-continued

| First Measurement | | | | | | | | | |
|---|---|---|---|---|---|---|---|---|---|
| 4.94 | 4.96 | 4.97 | 4.99 | 5.00 | 5.01 | 5.03 | 5.04 | 5.06 | 5.07 |
| 4.95 | 4.96 | 4.98 | 4.99 | 5.00 | 5.01 | 5.02 | 5.04 | 5.05 | 5.06 |
| 4.96 | 4.97 | 4.98 | 4.99 | 5.00 | 5.01 | 5.02 | 5.03 | 5.04 | 5.05 |
| 4.97 | 4.98 | 4.98 | 4.99 | 5.00 | 5.01 | 5.02 | 5.02 | 5.03 | 5.04 |
| 4.98 | 4.98 | 4.99 | 4.99 | 5.00 | 5.01 | 5.01 | 5.02 | 5.02 | 5.03 |
| 4.98 | 4.99 | 4.99 | 5.00 | 5.00 | 5.00 | 5.01 | 5.01 | 5.02 | 5.02 |
| 4.99 | 4.99 | 5.00 | 5.00 | 5.00 | 5.00 | 5.00 | 5.01 | 5.01 | 5.01 |
| 5.00 | 5.00 | 5.00 | 5.00 | 5.00 | 5.00 | 5.00 | 5.00 | 5.00 | 5.00 |

To use the constraints from all measurement points the Least Square Method will be applied to equation (4).

Below in equation (5), measurement points are summed over.

$$\Sigma\{A(\cos\phi - 1) + B\sin\phi + x_0 E_x + y_0 E_y + E_t\}^2 = 0 \quad (5)$$

$\Sigma\alpha$ is used abbreviation for:

$$\sum_{i=1, j=1}^{n,m} \alpha_{ij}$$

With n number of rows and m number of columns of sensors.

Due to the measurement errors the equation cannot be assumed to be exactly zero. Therefore, the minimum of the left side of equation for $\phi$, $x_0$ and $y_0$ will be derived. In order to derive the minimum the partial derivations of equation (5), $\phi$, $x_0$ and $y_0$ will be calculated.

Below is the derivation for $\phi$:

$$\Sigma\left\{\begin{array}{l}[A(\cos\varphi - 1) + B\sin\varphi + x_0 E_x + y_0 E_y + E_t] \\ [-A\sin\varphi + B\cos\varphi]\end{array}\right\} = 0$$

With the approximation: $\cos\phi \approx 1$ and $\sin\phi \approx \phi$:
with the approximation: $\cos\phi \approx 1$ and $\sin\phi \approx \phi$:

$$\Sigma\{B\phi + x_0 E_x + y_0 E_y + E_t\}\{-A\phi + B\} = 0 \Rightarrow$$

In Equation (6):

$$-\phi^2\Sigma(AB) + [\Sigma(BE_x) - \phi\Sigma(AE_x)]x_0$$
$$+ [\Sigma(BE_y) - \phi\Sigma(AE_y)]y_0$$
$$+ [\Sigma B^2 - \Sigma(AE_t)]\phi + \Sigma(BE_t) = 0 \quad (6)$$

The derivation for $x_0$ and $y_0$ are sown in equations (7) and (8) below. These two equations (7) and (8) can be used to calculate $x_0$ and $y_0$ in dependence from $\phi$ only these results can then be used to determine $\phi$ using equation (6).

$$\phi\Sigma(E_x B) + x_0\Sigma(E_x)^2 + y_0\Sigma(E_x E_y) + \Sigma(E_x E_t) = 0 \quad (7)$$

$$\phi\Sigma(E_y B) + x_0\Sigma(E_x E_y) + y_0\Sigma(E_y)^2 + \Sigma(E_y E_t) = 0 \quad (8)$$

$x_0$ and $y_0$ in dependence of $\phi$ only are shown below in equations (9) and (10).

$$x_0 = \left\{\frac{-\varphi\{\Sigma(E_y)^2\Sigma(E_x B) - \Sigma(E_x E_y)\Sigma(E_y B)\}}{\Sigma(E_x)^2\Sigma(E_y)^2 - [\Sigma E_x E_y]^2}\right\} - \quad (9)$$

$$\frac{\Sigma(E_y)^2\Sigma(E_x E_t) - \Sigma(E_x E_y)\Sigma(E_y E_t)}{\Sigma(E_x)^2\Sigma(E_y)^2 - [\Sigma E_x E_y]^2}$$

$$y_0 = \left\{ \frac{-\varphi\{\Sigma(E_xE_y)\Sigma(E_xB) - \Sigma(E_x)^2\Sigma(E_yB)\}}{[\Sigma E_xE_y]^2 - \Sigma(E_x)^2\Sigma(E_y)^2} \right\} - \qquad (10)$$

$$\frac{\Sigma(E_xE_y)\Sigma(E_yE_t) - \Sigma(Ex)^2\Sigma(E_yE_t)}{[\Sigma E_xE_y]^2 - \Sigma(E_x)^2\Sigma(E_y)^2}$$

Figure 14:
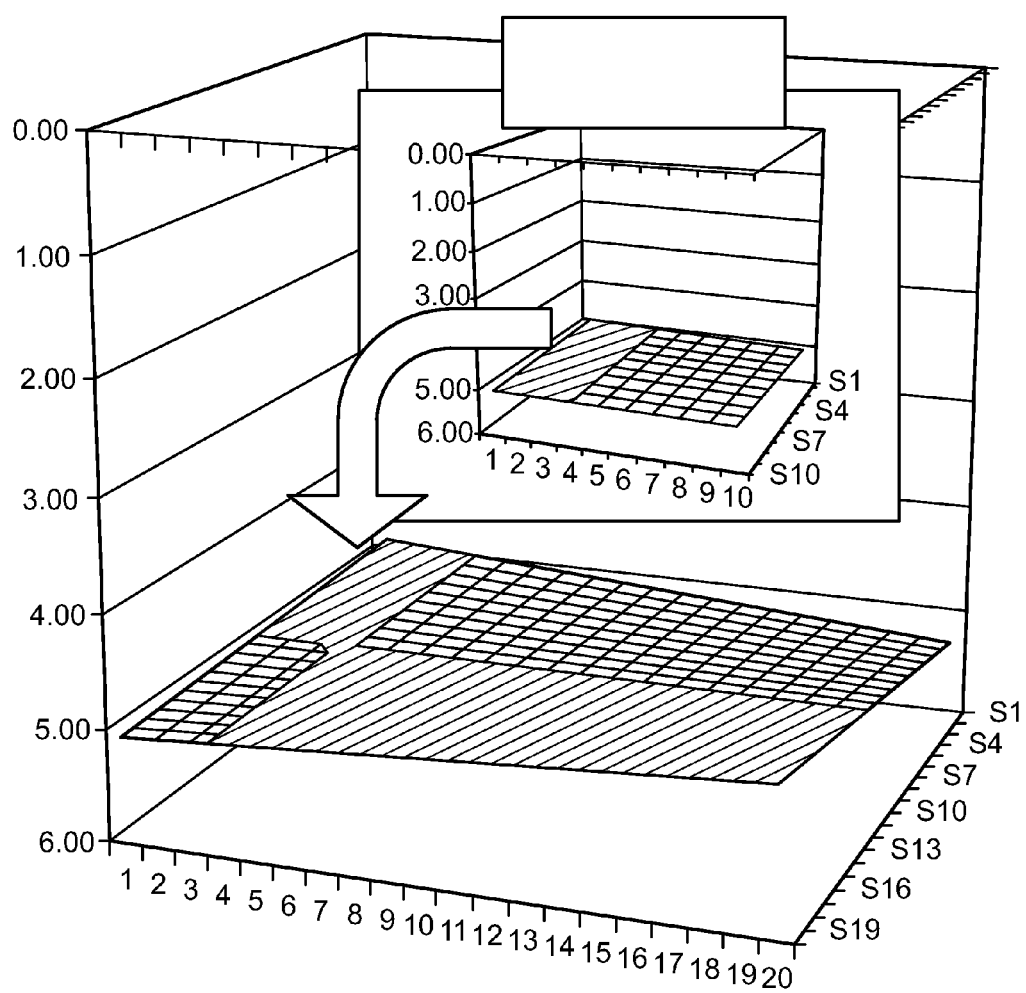
FIG. 14: shows a graphical simulation of corroded plate moved underneath a sensor array.

FIG. 14, shows a graphical simulation of the "corroded" plate is moved (translation and rotation) underneath the Sensor Array (mathematically easier versus moving the Sensor Array).

Figure 15:
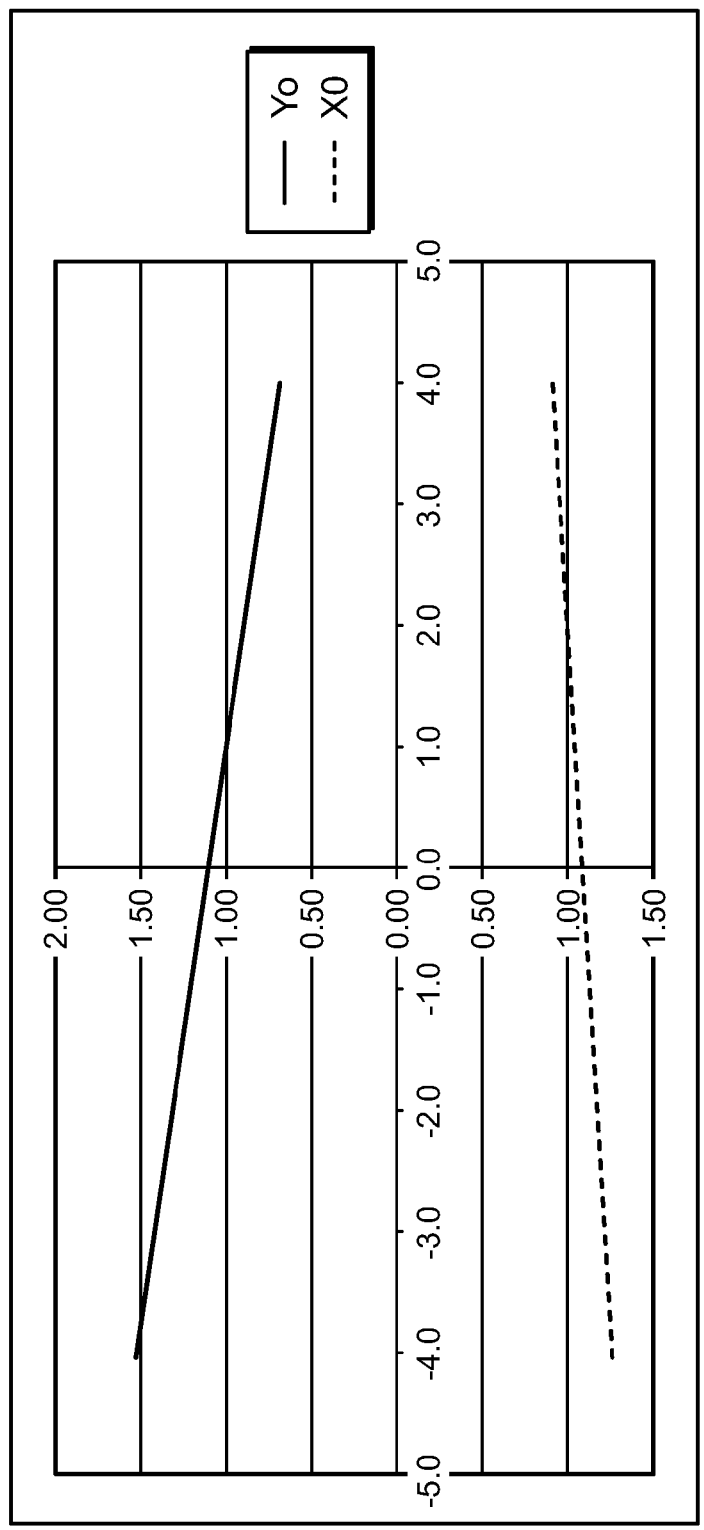
FIG. 15: shows a graphical depiction of initial $x_0$ and $y_0$ positions of a sensor dependent upon rotational angle.

FIG. 15 shows a graphical depiction of initial $x_0$ and $y_0$ positions of a sensor dependent upon rotational angle. Due to the complexity of the equations, a numerical solution was chosen. All sums have been realized as excel tables. For $x_0$ and $y_0$ (equations (9) and (10)), a table illustrated in FIG. 15 in dependence form φ has been generated ($-4°\leq\phi\leq 4°$) with a resolution of a tenth of a degree.

Figure 16:
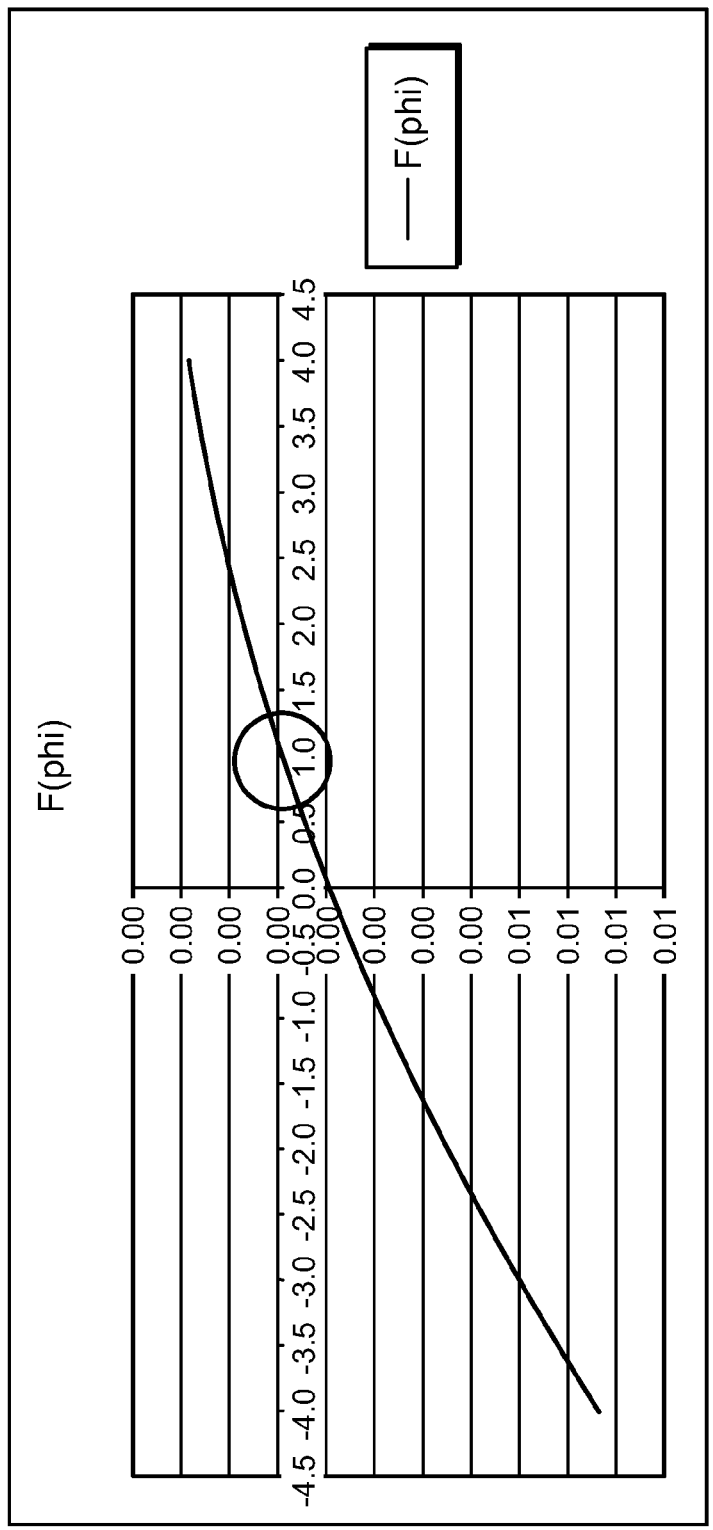
FIG. 16: shows a graphical solution for initial $x_0$ and $y_0$ positions of a sensor using rotational angle.

FIG. 16 shows a graphical solution of initial $x_0$ and $y_0$ positions of a sensor using rotational angle. The zero crossing in FIG. 16 gives the result for φ, which can be used to obtain $x_0$ and $y_0$.

Below in Tables 6-13, are examples from an excel simulations. Of course the accuracy is best when the movement is small. That means in practice that the measurement reputation frequency has to be high enough.

TABLE 6

| INPUT | |
|---|---|
| X0 Start | 0.00 |
| Y0 Start | 0.00 |
| Phi Start | 0.00 |
| X0 = | −0.50 |
| Y0 = | −0.50 |
| Phi = | −0.50 |

TABLE 7

| CALCULATION | | |
|---|---|---|
| Calc | Delta | % |
| −0.51 | −0.01 | 3% |
| 0.51 | 0.01 | 2% |
| 0.52 | 0.02 | 4% |

TABLE 8

| INPUT | |
|---|---|
| X0 Start | 0.00 |
| Y0 Start | 0.00 |
| Phi Start | 0.00 |
| X0 = | −0.50 |
| Y0 = | 1.00 |
| Phi = | 1.00 |

TABLE 9

| CALCULATION | | |
|---|---|---|
| Calc | Delta | % |
| −0.53 | −0.03 | 6% |
| 1.01 | 0.01 | 1% |
| 1.09 | 0.09 | 9% |

TABLE 10

| INPUT | |
|---|---|
| X0 Start | 0.00 |
| Y0 Start | 0.00 |
| Phi Start | 0.00 |
| X0 = | −2.00 |
| Y0 = | 2.00 |
| Phi = | 1.00 |

TABLE 11

| CALCULATION | | |
|---|---|---|
| Calc | Delta | % |
| −2.04 | −0.04 | 2% |
| 2.00 | 0.00 | 0% |
| 1.09 | 0.09 | 9% |

TABLE 12

| INPUT | |
|---|---|
| X0 Start | 0.00 |
| Y0 Start | 0.00 |
| Phi Start | 0.00 |
| X0 = | −2.00 |
| Y0 = | 2.00 |
| Phi = | 1.50 |

TABLE 13

| CALCULATION | | |
|---|---|---|
| Calc | Delta | % |
| −1.93 | 0.07 | −4% |
| 1.97 | −0.03 | −1% |
| −1.37 | 0.13 | −9% |

Alternatively, to the numerical solution an algebraic solution can be used. The equation for $x_0$ (9) and $y_0$ (10) can be understood in equation (11) as straight lines with:

$$x_0 = m_x\phi + b_x \text{ and } y_0 = m_y\phi + b_y \qquad (11)$$

With:

$$m_x = -\frac{\Sigma(E_y)^2\Sigma(E_xB) - \Sigma(E_xE_y)\Sigma(E_yB)}{\Sigma(E_x)^2\Sigma(E_y)^2 - [\Sigma E_xE_y]^2}$$

$$b_x = -\frac{\Sigma(E_y)^2\Sigma(E_xB_t) - \Sigma(E_xE_y)\Sigma(E_yE_t)}{\Sigma(E_x)^2\Sigma(E_y)^2 - [\Sigma E_xE_y]^2}$$

$$m_y = -\frac{\Sigma(E_xE_y)\Sigma(E_xB) - \Sigma(E_x)^2\Sigma(E_yB)}{[\Sigma E_xE_y]^2 - \Sigma(E_x)^2\Sigma(E_y)^2}$$

$$b_y = -\frac{\Sigma(E_xE_y)\Sigma(E_xE_t) - \Sigma(E_x)^2\Sigma(E_yE_t)}{[\Sigma E_xE_y]^2 - \Sigma(E_x)^2\Sigma(E_y)^2}$$

Applying equation (11) to equation (6) results in the following quadratic equation:

$$\{\Sigma(AB) + m_x\Sigma(AE_x) \circ m_y\Sigma(AE_y)\}\phi^2$$

$$-\{m_x\Sigma(BE_x) - b_x\Sigma(AE_x) + m_y\Sigma(BE_y) - b_y\Sigma(AE_y) + \Sigma B^2 - \Sigma(AE_t)\}\phi$$

$$-b_x\Sigma(BE_x) - b_y\Sigma(BE_y) - \Sigma(BE_t) = 0$$

Tables 14-17 below provide examples of different "corrosion" simulations.

TABLE 14

| INPUT | |
|---|---|
| X0 Start | 0.00 |
| Y0 Start | 0.00 |
| Phi Start | 0.00 |
| X0 = | 0.80 |
| Y0 = | 0.90 |
| Phi = | −0.60 |

TABLE 15

| CALCULATION | | |
|---|---|---|
| Calc | Delta | % |
| 0.82 | 0.20 | 2.6% |
| 0.88 | −0.20 | −2.3% |
| −0.60 | 0.00 | 0.0% |

TABLE 16

| INPUT | |
|---|---|
| X0 Start | 0.00 |
| Y0 Start | 0.00 |
| Phi Start | 0.00 |
| X0 = | −2.90 |
| Y0 = | −2.30 |
| Phi = | 1.90 |

TABLE 17

| CALCULATION | | |
|---|---|---|
| Calc | Delta | % |
| −2.92 | −0.02 | 0.7% |
| −2.29 | 0.01 | −0.5% |
| 1.89 | −0.01 | −0.3% |

If the evaluation of rotation is not needed, the evaluation of the position of the sensor array is much easier. In this case, the assumption can be taken that all sensors within the array move exactly the same way. (See "Determining Constant Optical Flow," Berhold K. P. Horn, 2003).

$$E_x x + E_y y + E_t = 0$$

Using the Least Square Method as described above determines the movement in the x and y direction (see examples in Tables 18-21 below). The accuracy is higher compared with the solution for translation plus rotation.

TABLE 18

| INPUT | |
|---|---|
| X0 Start | 0.00 |
| Y0 Start | 0.00 |
| X0 = | −1.20 |
| Y0 = | 1.50 |

TABLE 19

| CALCULATION | | | |
|---|---|---|---|
| | Calc | Delta | % |
| x = | −1.20 | 0.00 | 0% |
| y = | 1.50 | 0.00 | 0% |

TABLE 20

| INPUT | |
|---|---|
| X0 Start | 0.00 |
| Y0 Start | 0.00 |
| X0 = | −3.00 |
| Y0 = | 2.50 |

TABLE 21

| CALCULATION | | | |
|---|---|---|---|
| | Calc | Delta | % |
| x = | −3.00 | 0.00 | 0% |
| y = | 2.50 | 0.00 | 0% |

The above explanation describes the sensor array for navigation on surfaces and/or many of its advantages. As the form described here is only an embodiment which serves the explanation, however, it can be seen that various changes to the form, the construction and/or the arrangement of the components can be undertaken without departing from the subject or the scope of the claims and without losing the fundamental advantages. Changes of this type should be included in the protective scope of the following claims.

The invention claimed is:

1. Device for nondestructive determination of a rotational movement on a surface of a specimen, comprising:
   a. a transmitter configured to transmit a temporal sequence of excitation signals Si adapted to penetrate into the specimen at least to some extent and interact with corrosion of the specimen,
   b. an array comprising a plurality of receivers configured to receive echo signals, which result from the interaction of the excitation signals Si transmitted by the transmitter with said corrosion, wherein the echo signals for one of the excitation signals Si, which are absorbed by the plurality of receivers, form a set M (Si) of measurement values, and
   c. an evaluation unit configured to determine a rotational movement of the array on the surface from a plurality of measurement value sets M (Si) which are correlated with temporally sequential excitation signals Si.

2. Device according to claim 1, wherein the excitation signals are adapted to interact with structural characteristics of the specimen.

3. Device according to claim 2, wherein the structural characteristics include at least one of a geometric structure of a boundary surface of the specimen or a material inhomogeneity in a volume of the specimen.

4. Device according to claim 1, wherein the receivers which form the array are arranged lying in one plane.

5. Device according to claim 1, wherein the transmitter and the receivers are mechanically combined in a probe.

6. Device according to claim 1, wherein at least one of the plurality of the receivers is configured to also be operated as a transmitter for transmitting the temporal sequence of excitation signals Si.

7. Device according to claim 6, wherein a plurality of the receivers of the array are configured as transmitters.

8. Device according to claim 7, wherein the excitation signals Si are in each case created by the plurality of the receivers of the array that are configured as transmitters.

9. Device according to claim 1, wherein the array comprises at least two linear arrangements, each of the arrangements having at least three of said receivers, which receivers extend in multiple spatial directions.

10. Device according to claim 1, wherein the receivers which form the array are arranged on grid points of a two-dimensional array, wherein at least three receivers are arranged in each of the two main directions of the grid.

11. Device according to claim 1, wherein the receivers comprise at least one of ultrasound receivers, eddy current sensors, piezoelectric sensors, magnetic field sensors and sensors for electromagnetic radiation.

12. Device according to claim 1, wherein the evaluation unit is further configured to also determine a translational movement of the array on the surface of the specimen from the plurality of measurement value sets M (Si).

13. Device according to claim 1, wherein some of the receivers are used for positional data and at least one other of the receivers is used for measuring said corrosion.

14. Test unit for a spatially resolved determination of a structural characteristic of a specimen, comprising:
   a. a transmitter configured to transmit a temporal sequence of excitation signals Si adapted to penetrate into the specimen at least to some extent and interact with corrosion of the specimen,
   b. an array comprising a plurality of receivers configured to receive echo signals, which result from the interaction of the excitation signals Si, transmitted by the transmitter with said corrosion, wherein the echo signals for one of the excitation signals Si, which are absorbed by the plurality of receivers, form a set M (Si) of measurement values, and
   c. an evaluation unit configured to determine a rotational movement of the array on a surface of the specimen from a plurality of measurement value sets M (Si) which are correlated with temporally sequential excitation signals Si,
   wherein the test unit is configured to create an image of a spatial distribution of the corrosion from movement data recorded by the test unit as well as the measurement value sets M (Si).

15. Test unit according to claim 14, wherein the movement data relates to both the rotational movement and a translational movement of the array on the surface of the specimen.

16. Test unit according to claim 14, wherein the test unit is configured to show the image created of the spatial distribution of the corrosion on a display unit.

17. Test unit according to claim 14, wherein some of the receivers are used for positional data and at least one other of the receivers is used for measuring said corrosion.

18. Test unit according to claim 14, wherein the test unit is configured to create the image of the spatial distribution of the corrosion within a created image of the specimen as designed or manufactured.

19. Method for a nondestructive determination of a rotational movement of an array on a surface of a specimen, comprising the following steps:
   a. transmission of a temporal sequence of excitation signals Si adapted to penetrate into the specimen at least to some extent and interact with corrosion of the specimen,
   b. reception of echo signals, which result from the interaction of the transmitted excitation signals Si with said corrosion, by means of an array comprising a plurality of receivers, wherein the echo signals for one of the excitation signals Si, which are absorbed by the plurality of receivers, form a set M (Si) of measurement values, and
   c. determination of a rotational movement of the array on the surface of the specimen from a plurality of measurement value sets M (Si) which are correlated with temporally sequential excitation signals Si.

20. Method according to claim 19, wherein the excitation signals are adapted to interact with structural characteristics of the specimen.

21. Method according to claim 20, comprising the following further method step:
   a. Creation of an image of a spatial distribution of the corrosion from determined movement data as well as the measurement value sets M (Si).

22. Method according to claim 21, wherein the movement data relates to both the rotational movement and a translational movement of the array on the surface of the specimen.

23. Method according to claim 21, comprising the following further step:
   a. Display of the image created of the spatial distribution of the corrosion on a display unit.

24. Method according to claim 21, wherein the creation step includes creation of the image of the spatial distribution of the corrosion within a created image of the specimen as designed or manufactured.

25. Method according to claim 20, wherein the structural characteristics include at least one of a geometric structure of a boundary surface of the specimen or a material inhomogeneity in a volume of the specimen.

26. Method according to claim 19, wherein the receivers which form the array are arranged lying in one plane.

27. Method according to claim 19, wherein at least one of the plurality of receivers is configured to also be operated as a transmitter for transmitting the temporal sequence of excitation signals Si.

28. Method according to claim 27, wherein a plurality of the receivers of the array are configured as transmitters.

29. Method according to claim 28, wherein the excitation signals Si are in each case created by the plurality of the receivers of the array that are configured as transmitters.

30. Method according to claim 19, wherein the array comprises at least two linear arrangements, each of the arrangements having at least three of said receivers, which receivers extend in multiple spatial directions.

31. Method according to claim 19, wherein the receivers which form the array are arranged on grid points of a two-dimensional array, wherein at least three of said receivers are arranged in each of the two main directions of the grid.

32. Method according to claim 19, wherein the receivers comprise at least one of ultrasound receivers, eddy current sensors, piezoelectric sensors, magnetic field sensors or sensors for electromagnetic radiation.

33. Method according to claim 19, comprising the following further step:
   a. Determination of a translational movement of the array on the surface of the specimen from the plurality of measurement value sets M (Si).

34. Method according to claim 19, further comprising using some of the receivers for positional data and using at least one other of the receivers to measure said corrosion.

35. Device for a nondestructive creation of an image of a spatial distribution of a structural characteristic of a specimen, comprising:
   a. a first transmitter configured to transmit a temporal sequence of excitation signals P adapted to penetrate into the specimen at least to some extent and interact with corrosion of the specimen,
   b. a first receiver configured to absorb the excitation signals P transmitted by the first transmitter as echo signals after interaction with said corrosion,
   c. a second transmitter configured to transmit a temporal sequence of excitation signals Si adapted to interact with the specimen,
   d. an array comprising a plurality of second receivers configured to receive echo signals, which result from interaction of the excitation signals Si transmitted by the second transmitter with the specimen, wherein the echo signals for one of the excitation signals Si, which are absorbed by the second receivers, form a set M (Si) of measurement values,
   e. an evaluation unit configured to determine a movement of the array on a surface of the specimen from a plurality of measurement value sets M (Si) which are correlated with temporally sequential excitation signals Si of the second transmitter, and
   f. a visualization unit configured to create an image of the spatial distribution of the corrosion from the movement of the array on the surface of the specimen recorded by the evaluation unit as well as from the echo signals received by the first receiver.

36. Device according to claim 35, wherein the first and second transmitters are identical.

37. Device according to claim 35, wherein the first receiver and one of the second receivers are identical.

38. Device according to claim 35, wherein the first transmitter and the first receiver are identical.

39. Device according to claim 35, wherein the second transmitter and one of the second receivers are identical.

40. Device according to claim 35, wherein the visualization unit is configured to create the image of the spatial distribution of the corrosion within a created image of the specimen as designed or manufactured.

41. Device for a spatially resolved determination of a structural characteristic of a specimen, comprising:
   a. a first transmitter configured to transmit a temporal sequence of excitation signals Si adapted to penetrate into the specimen at least to some extent and interact with the specimen,
   b. an array comprising a plurality of first receivers configured to receive echo signals, which result from the interaction of the excitation signals Si, transmitted by the first transmitter, with the specimen, wherein the echo signals for one of the excitation signals Si, which are absorbed by the receivers, form a set M (Si) of measurement values, and
   c. an evaluation unit configured to determine a rotational movement of the array on a surface of the specimen from a plurality of measurement value sets M (Si) which are correlated with temporally sequential excitation signals Si of the first transmitter,
   wherein the device is configured to create an image of a spatial distribution of the structural characteristic of the specimen from movement data recorded by the device as well as the measurement value sets M (Si), within a created image of the specimen as designed or manufactured.

42. Device according to claim 41, wherein:
the device further comprises:
   a. a second transmitter configured to transmit a temporal sequence of excitation signals P adapted to penetrate into the specimen at least to some extent and interact with the structural characteristic of the specimen, and
   b. a second receiver configured to absorb the excitation signals P transmitted by the second transmitter as echo signals after an interaction with the specimen, and
the device is configured to create said image by including a visualization unit configured to create the image of the spatial distribution of the structural characteristic of the specimen from the movement of the array on the surface of the specimen recorded by the evaluation unit as well as from the echo signals received by the second receiver.

43. Device according to claim 41, wherein the device is further configured to create the image of the specimen as designed or manufactured from a graphics, image or CAD file.

44. Device according to claim 43, wherein the device is further configured to save data about the structural characteristic into said file.

45. Device according to claim 44, wherein said data includes a position of the structural characteristic in the specimen.

46. Method for a nondestructive determination of a rotational movement of an array on a surface of a specimen, comprising the following steps:
   a. transmission of a temporal sequence of excitation signals Si adapted to penetrate into the specimen at least to some extent and interact with the specimen,
   b. reception of echo signals, which result from the interaction of the transmitted excitation signals Si with the specimen, by means of an array comprising a plurality of receivers, wherein the echo signals for one of the excitation signals Si, which are absorbed by the receivers, form a set M (Si) of measurement values,
   c. determination of a rotational movement of the array on the surface of the specimen from a plurality of measurement value sets M (Si) which are correlated with temporally sequential excitation signals Si, and
   d. creation of an image of a spatial distribution of a structural characteristic of the specimen from determined movement data as well as measurement value sets M (Si), within a created image of the specimen as designed or manufactured.

47. Method according to claim 46, further comprising creation of the image of the specimen as designed or manufactured from a graphics, image or CAD file.

48. Method according to claim 47, further comprising saving data about the structural characteristic into said file.

49. Method according to claim 48, wherein said data includes a position of the structural characteristic in the specimen.

* * * * *